(12) United States Patent
Depeursinge et al.

(10) Patent No.: US 7,164,812 B2
(45) Date of Patent: Jan. 16, 2007

(54) OPTICAL WAVEGUIDE SENSOR SYSTEM

(75) Inventors: Christian Depeursinge, Preverenges (CH); Daniel Salzmann, Les Genevez (CH)

(73) Assignee: Linde Medical Sensors AG, Basel (CH)

( * ) Notice: Subject to any disclaimer, the term of this patent is extended or adjusted under 35 U.S.C. 154(b) by 54 days.

(21) Appl. No.: 10/488,171

(22) PCT Filed: Sep. 3, 2002

(86) PCT No.: PCT/EP02/09837

§ 371 (c)(1),
(2), (4) Date: Mar. 5, 2004

(87) PCT Pub. No.: WO03/023374

PCT Pub. Date: Mar. 20, 2003

(65) Prior Publication Data

US 2004/0240768 A1    Dec. 2, 2004

(30) Foreign Application Priority Data

Sep. 5, 2001    (EP) ................................. 01810856

(51) Int. Cl.
*G02B 6/00*    (2006.01)
(52) U.S. Cl. .......................................... 385/12; 385/14
(58) Field of Classification Search .................. 385/12, 385/14
See application file for complete search history.

(56) References Cited

U.S. PATENT DOCUMENTS

| | | | |
|---|---|---|---|
| 5,289,256 A | 2/1994 | Gramling et al. ............ 356/345 |
| 5,394,239 A | 2/1995 | Valette ........................ 356/345 |
| 5,903,685 A * | 5/1999 | Jones et al. .................... 385/12 |
| 2002/0172457 A1* | 11/2002 | Tapalian et al. ............... 385/30 |
| 2002/0191935 A1* | 12/2002 | Gao ............................ 385/132 |
| 2003/0012479 A1* | 1/2003 | Kitou et al. ................... 385/14 |
| 2004/0076372 A1* | 4/2004 | Philipsen et al. .............. 385/24 |
| 2004/0081384 A1* | 4/2004 | Datesman et al. ............. 385/12 |

OTHER PUBLICATIONS

Weibin Huang and Richard R.A. Syms, "Analysis of Folded Erbium-Doped Planar Waveguide Amplifiers by the Method of Lines," Journal of Lightwave Technology, vol. 17, No. 12, Dec. 1999, 15 pages.

G.N. van den Hoven, et al., "Net optical gain at 1.53 μm in Er-doped $Al_2O_3$ waveguides on silicon," Appl. Phys. Lett. 68, (14), Apr. 1, 1996.

G. Pandraud, et al. "Evanescent wave sensing: new features for detection in small volumes," Sensors and Actuators 85 (2000) pp. 158-162.

* cited by examiner

*Primary Examiner*—Ellen E. Kim
(74) *Attorney, Agent, or Firm*—Brian S. Steinberger; Law Offices of Brian S. Steinberger, P.A.

(57) ABSTRACT

The sensor system for the detection of chemical substances has a spiral optical waveguide which produces an evanescent field penetrating into the adjacent medium, a light source for coupling light into the waveguide, and a detecting circuit for receiving light from the waveguide and producing an output signal reflecting the sensed chemical substance. The waveguide has the form of a bifilar, non-crossing spiral. It consists of an incoming or decreasing spiral segment and an outgoing or increasing spiral segment continuously bound by a central semi-circular segment.

15 Claims, 4 Drawing Sheets

OPTICAL WAVEGUIDE SENSOR SYSTEM

Figure 1:
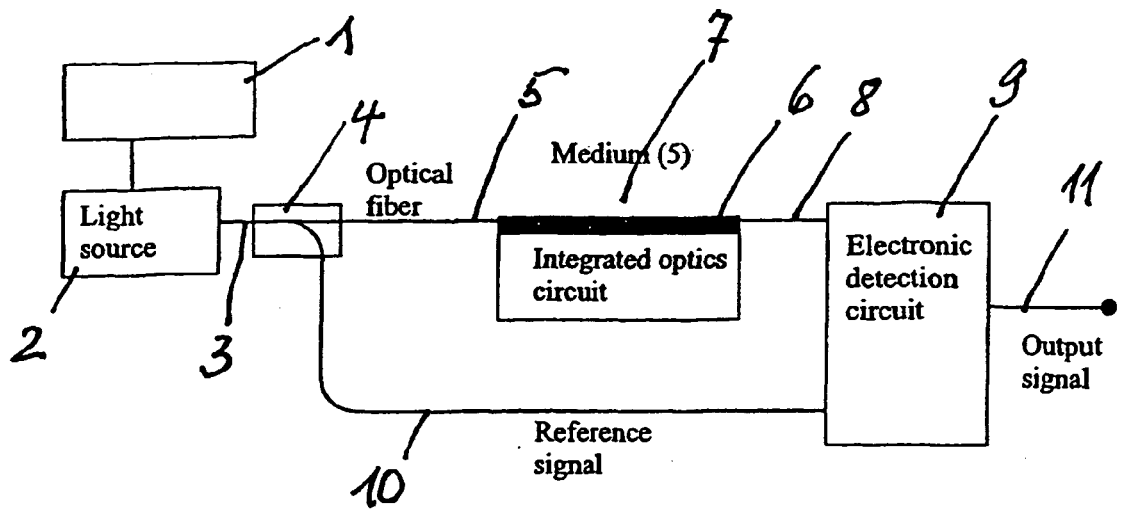

The present invention concerns a sensor system for the detection of chemical substances in an adjacent medium, with an optical waveguide adapted to produce an evanescent field for penetrating into the adjacent medium, light source means for coupling light into the waveguide, and detector means for receiving light from the waveguide and producing an output signal reflecting the sensed chemical substance.

The general aim of the present invention is the detection of gas or liquid concentrations, especially in the presence of a gas or liquid mixture. More particularly, the present invention is directed to the field of gas permeation, mainly in the medical field where transcutaneous blood gases are to be detected, e.g. carbon dioxide, oxygen and possibly anaesthetic gases within the blood. Such gases permeate through the patient skin at very low flow rate.

According to the most well-known detection methods the interaction between the light and the detected medium usually occurs in a free-space cell which can be a single- or a multi-pass cell depending on whether the cell facets are reflecting light or not. Most of the systems make use of an optical cell through which the analyte is flowing and in which the whole light beam interacts with the medium molecules. In the last decades systems using fiber optic evanescent field detection have been proved but interaction length and reliability are the main limitations of such systems for industrial application.

It is also well known that integrated waveguides can be applied as chemical sensors using evanescent field interaction. Thus reference may be made to Lambeck, P. V. in "Sensors and actuators B", vol.8, 1992, p. 103–116, where mainly two properties of the detected medium, spectral absorption and refractive index which are combined in a complex dielectric constant, interact within the evanescent field on an integrated optical waveguide.

Further reference may be made to Pandraud, G. et al. in "Sensors and actuators B", Chemical 85, 2000, p.158–162 where evanescent wave sensing is described with an accent on optical absorption of the detected medium applying the Lambert-Beer law as read-out principle and micro-fluidic direct bonding for sampling cell miniaturization. The resulting cell volume is about 200 µm·400 µm·1 cm=0.8 mm$^3$ and is well adapted to micro-fluidic analysis.

But as mentioned before, the present invention generally aims at detecting chemicals in very small volumes or permeating through membranes. In the case of transcutaneous blood gas detection the gas permeates through the patient skin at flow rates of approximately 1 µl·cm$^{-2}$·min$^{-1}$. With such flow rates a volume of 0, 8 mm$^3$ over a 400 µm·1 cm surface would rise the response time to 20 min which is two orders of magnitude too high for transcutaneous gas detection.

As a possible solution of this problem it has been considered to increase the interaction length but especially within a small sensing surface in the order of one square centimeter.

In the prior art specific waveguide curvatures and geometries performing high packing density have been proposed: WO 9400750 shows two waveguide geometries performing dense interaction length per unit area, one in a zigzag shape and one in a spiral shape. The principle uses spectral analysis, at the output, of an injected coded bundle or light pulse. The proposed zigzag waveguide exhibits a clear disadvantage as the waveguide occupation fraction rises as the zigzag curvature becomes strong. The limit is reached as the curvature losses become critical but this limit is reached for each zigzag leading to strong total losses as the waveguide occupation fraction is optimized. The proposed spiral waveguide is characterized by a relative short distance between two adjacent segment inducing voluntary cross-coupling. In addition the central ends of the enlaced spiral do not form a continuous waveguide.

A spiral shape detector is also shown in U.S. Pat. No. 5,394,239. The goal of the patent is to integrate on a chip an interferometric sensor. It is constituted by a double enlaced spiral waveguide with crossings of all individual windings to get out from the center of the spiral. The crossings consist of a bridge requiring multiple masks so that the process time/cost is relatively high.

In GB 2 222 881 a detection principle is described which is a continuous signal (DC) detection using strong resonant waveguide, the spectrum of which is adjusted to match the line spacing of the absorption of the detected medium. In this case the sensitivity is enhanced by using a light source spectral width significantly larger than the absorption line width of the detected medium, ideally covering many absorption lines. Moreover the active stabilization of the resonance wavelength is required to maintain a good match of the resonance wavelength to the source wavelength if various lines of the detected gas. Moreover, a continuous signal detection (DC) in spectroscopy, which is sensitive to the absorption baseline fluctuations, is much more noisy than the detection of a modulated signal (AC) used in so-called "modulation spectroscopy" which, on the contrary, guarantees a perfect absorption baseline rejection.

In view of the above the present invention has the object of providing a sensor system which is free from the disadvantages of the known sensor systems.

According to the invention high packing densities and sensitivities are achieved by a sensor system in which the waveguide has the form of a bifilar, non-crossing spiral consisting of an incoming or decreasing spiral segment and an outgoing or increasing spiral segment continuously bound by a central semi-circular segment.

For the purpose of this specification the term bifilar is used in the basic meaning of involving a single thread doubled back upon itself. The term is not supposed to include a configuration with threads twisted about each other.

Aside from the use in the medical field, especially for transcutaneous blood gas measurement the sensor system according to the invention is applicable in the fields of gas analysis, monitoring of gas production and in microstructure processing, automotive, environmental and food industries etc.

The fact that sensors according to the present invention are constituted by non-crossing waveguides reduces the number of masks needed for processing to a minimum. The detection principle does not use interference signals so that the chemical refractive index variation exhibited by chemical mixtures, does not influence the measurement signal.

According to a preferred embodiment of the invention a wavelength modulation spectroscopy technique is used which provides a rejection of the absorption baseline fluctuations leading to an enhanced molecule selectivity and sensitivity in chemical mixture.

Figure 2:
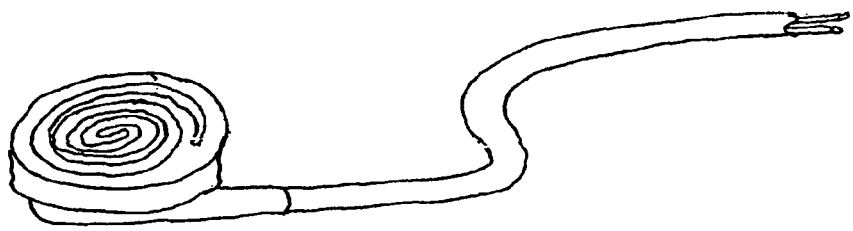
Figure 3:
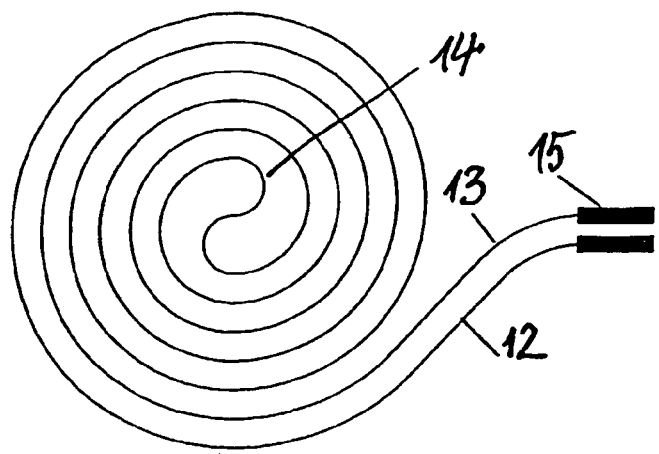
Figure 4:
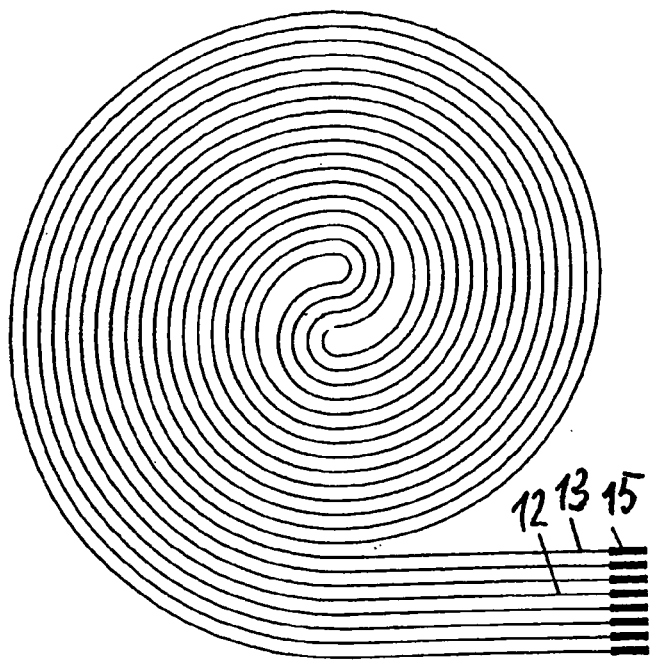
Figure 5:
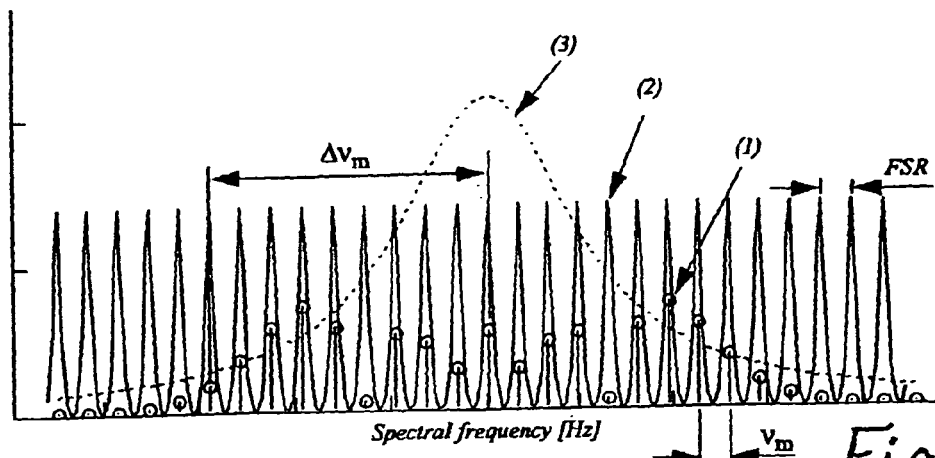
Figure 6A:
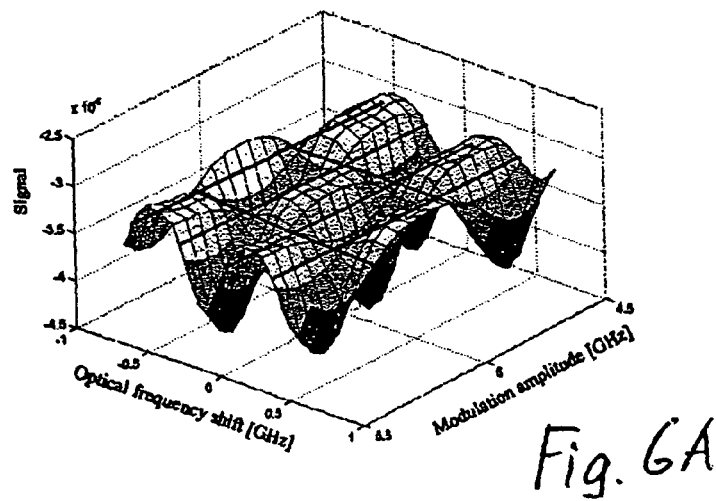
Figure 6B:
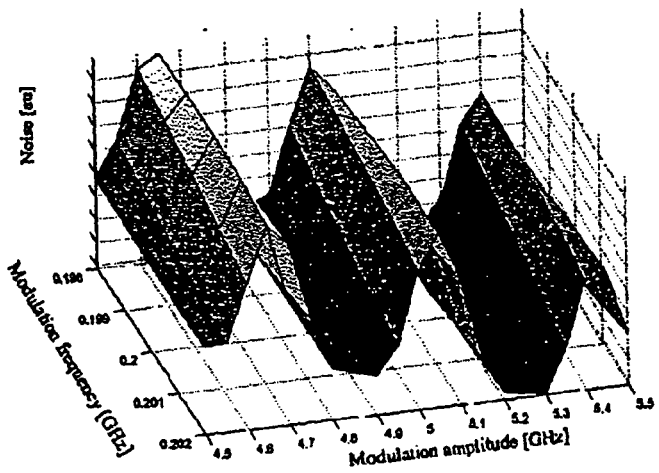
Figure 7:
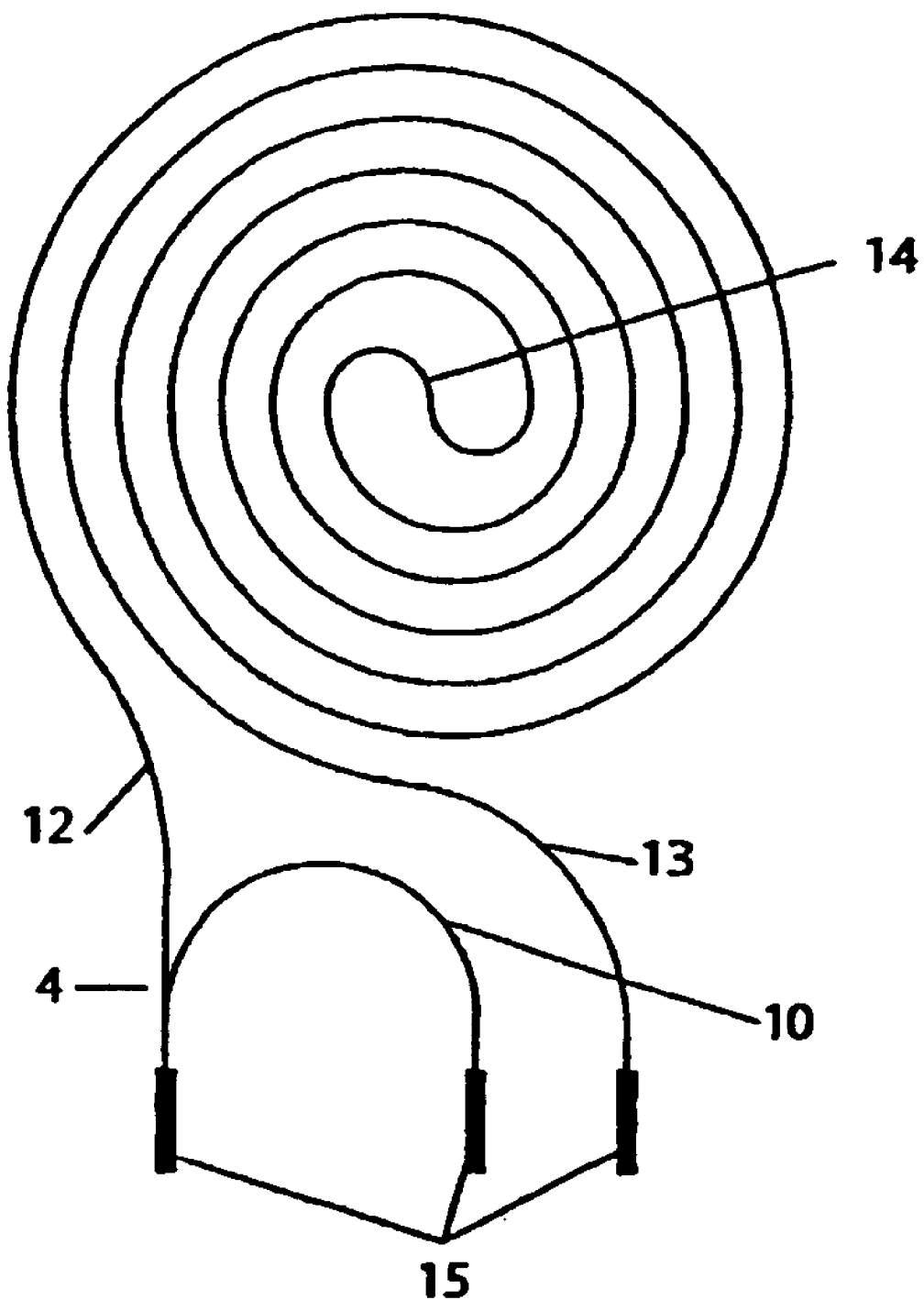

In the following a preferred embodiment of the invention is described with regard to the accompanying drawings in which FIG. 1 shows a schematic diagram of a sensor system FIG. 2 shows a cross-section of the sensor portion FIG. 3 shows a typical geometry of a sensor waveguide FIG. 4 shows an alternative waveguide geometry FIG. 5 shows a diagram of the resonant cavity signal enhancement FIG. 6 shows a scan diagram of modulation parameters FIG. 7 shows an extension of the integrated optics circuit including the power splitter The sensor system shown in FIG. 1 uses an integrated optical waveguide for evanescent wave sensing of the surrounding medium and a technique of wavelength modulation for spectroscopy. A signal generator 1 is connected to a light source 2 whereby the so-called signal generator effects a wavelength modulation as described in the following general equation for sine modulation:

$$I_{opt} \propto E \cdot E^* \text{ and } E_{LD}(t) \propto$$

$$\sqrt{1 + M \cdot \cos(2\pi \cdot v_m \cdot t + \varphi)} \cdot e^{i\left(2\pi \cdot v_0 \cdot t + \frac{\Delta v_m}{v_m} \cdot \sin(2\pi \cdot v_m \cdot t)\right)}$$

where $I_{opt}$ and E are respectively the optical intensity and the optical field generated by the light source 2, M is the intensity modulation index, $v_m$ is the modulation frequency, t the time, $\varphi$ the phase-lag between intensity modulation and optical frequency modulation, $\Delta v_m$ represents the optical frequency-modulation amplitude corresponding to the excursion of the optical frequency around the central optical frequency $v_0$.

The light source 2 is connected via an optical fiber 3 to a fibered coupler or optical power splitter 4 splitting the fiber into two output fibers. A first output fiber 5 is coupled to the input of an integrated optics waveguide 6.

This is effected by gluing or welding the corresponding optical fiber 5 into an integrated V-groove of the integrated optics circuit 6. The fiber optical field is adapted, using an integrated taper or a mode converter, to the waveguide propagation mode reducing the overall transmission losses and optical reflections at the waveguide ends.

Interferometric noise will be understood in this description as having the following origin: The interferometric noise results from time fluctuations of the detected signal. These fluctuations, which may appear as random, periodical or pseudo-periodical, result from the interference(s) of the multiply reflected and transmitted optical waves propagating in the optical circuitry. These reflections originate from the undesired changes of the refractive indexes and of the wave guide geometry along the optical path and from the connectors in the optical circuit. Optical cavities may result from these discontinuities, typically at the fluid cell facets (the waveguide ends in our case) and at the optical component interfaces. Periodical or pseudo-periodical resonances, which are sensitive to the cavity length $L_{cav}$ and refractive index $n_{cav}$ variations, appear and modulate the spectrum of the optical signal. The resonance period is called cavity free-spectral-range FSR and is defined as:

$$FSR = \frac{c}{2n_{cav}L_{cav}}$$

where c is the vacuum speed of light.

Hence, any changes in cavity length or refractive index will vary the cavity FSR which causes a shift of the q-th resonance of the cavity. The q-th resonance satisfies the following equation:

$$q\lambda = 2n_{cav}L_{cav}$$

where $\lambda$ is the optical wavelength of the light propagation throughout the cavity.

Consequently either a rapid shifting of the cavity spectrum or a wavelength change of the optical wave, as created in wavelength modulation spectroscopy, produces time fluctuations of the output signal called "interferometric noise".

The whole optical circuit has been designed in order to minimize the interferometric noise of the exciting and collecting fiber by elongating these fibers in such a way that the interferometric noise associated to these fibers can be eliminated by high frequency rejection and averaging. The most important part of the interferometric noise originate from the measurement waveguide itself, forming a cavity with resonances interfering severely with the gas spectral lines. The measurement waveguide length may be varied mainly by temperature and the waveguide effective refractive index may be influenced by the detected medium refractive index. The latter can undergo deep variations in the presence of gas mixture.

The amplitude of the interferometric noise is influenced by the optical reflections at the interfaces and discontinuities along the optical path. In particular, the sensing cavity formed by the integrated optics waveguide 6 is a source of interferometric noise which degrades the signal from the medium. Reducing the reflections at the waveguide ends contributes to reduce determinedly the interferometric noise.

Many types of light sources having a bandwidth narrower than the absorption lines of the analyzed medium can be used. Laser diodes, solid state lasers and fiber lasers are convenient. In a preferred embodiment, a DFB laser diode, stabilized in DC-current and temperature, is used as light source 1. The signal generator 2 is used to drive the current of the DFB diode. A modulation of the wavelength results from the current modulation. A ramp or sine or the superposition of both is generated by the signal generator resulting in a wavelength which is sinusoidally modulated around a central wavelength that can be ramped.

The waveguide 6 is produced using (but not restricted to) the known Si3N4/SiO2 technology on Si-substrate. The Si3N4/SiO2/Si high guidance technology has been optimized for evanescent wave sensitivity and propagation loss. It allows strong waveguide curvature leading to a very long spiral length (can be easily raised to 1 m length) on a typical 1 cm diameter substrate area.

The question of the choice of the optimal length of the measurement waveguide cannot be solved in any case. It results from a compromise between the needed interaction length and the severity of the losses which increases with length and attenuate the signal. So an optimal waveguide length can be found, which is a function of the propagation losses generally expressed in dB/cm. Using the present technology developments the optimal waveguide length has been found to be 14.5 cm for −0.3 dB/cm propagation loss.

At each end the waveguide 6 is provided with a V-groove for so-called fiber pigtailing (i.e. setting the position and helping for gluing or welding) and a taper or a mode converter. It performs the coupling and the transition from the optical fiber mode to the integrated waveguide mode. Moreover the waveguide ends can be angled for interferometric noise reduction (typical angles are in the order of 8°)

The integrated optics circuit corresponding to the waveguide 6 in the preferred embodiment shown in FIG. 1 can be extended so that an integrated version of the power splitter 4, shown in FIG. 7, is implemented. This solution allows a better compensation of the fluctuations of the fiber coupling and mode transition. Advantageously, an improved balanced detection can be achieved. Further implementations of parts of the system are not limited to the power splitter allowing a system miniaturization.

The output fiber 8 of the waveguide 6 is coupled to a first input of a symmetric electronic detection circuit 9. The second output fiber 10 of coupler 4 is directly coupled to a second input of the detection circuit 9.

The modulated light coming form the light source is split in coupler 4 into a measurement signal which is fed to the waveguide and a reference signal. The power of the reference signal may be adjusted by introducing a fibered optical attenuator (not shown). Both the reference signal and the output signal from the waveguide are compared according to a balanced detection principle in the electronic detection circuit 9.

The resulting signal at output 11 of the detection circuit represents the concentration of the gas/liquid detected in the medium 7 because the evanescent wave of the uncovered integrated waveguide 8 interacts within the medium 7.

The waveguide schematically shown in FIG. 3 is composed of an incoming segment 12 and an outgoing segment 13 bound continuously by a semi-circular segment 14. By this configuration a non-crossing spiral waveguide is formed. The distance between two adjacent segments is large enough to prevent cross-coupling. At the ends of the waveguide an integrated taper or mode converter 15 is implemented to improve coupling efficiency and to reduce the interferometric noise. As already mentioned, an integrated V-groove is implemented to ease the positioning and the gluing/welding of the corresponding optical fibers.

In order to enhance the system signal-to-noise ratio (SNR) two different methods are appropriate which concern the wavelength modulation technique (by the wavelength modulator (1)) of the light source (2), by the adjustment of the parameters of the wavelength modulator. One by tuning parameters on the waveguide resonance spectrum in order to enhance the signal and the other by tuning the parameters for interferometric noise rejection. For both methods the light source spectral width is narrow compared to the absorption line width.

The first method is based on the adjustment of the modulation frequency: the modulation frequency of the light source is made equal to a fraction or a multiple of the free-spectral-range (FSR) of the dominant cavity. The elimination of most of the refractive index steps along the optical path by a careful design of the optical circuit has the consequence that the measurement waveguide, for which the interfaces between the waveguide and the optical fibers (or waveguide ends) constitutes the dominant optical cavity, having resonances contributing strongly to the generation of the interferometric noise. The modulation frequency will be chosen according to the following formula:

$$\nu_m = FSR \cdot k (k=1, 2, 3 \ldots)$$

wherein $\nu_m$ corresponds to the wavelength modulation frequency in Hz and FSR is the optical cavity free-spectral-range in Hz.

Preferably, the cavity length is equal to the waveguide length (chosen for optimal sensitivity) and the cavity refractive index corresponds to the waveguide effective refractive index (in the order of around 1.6). With this choice of the modulating frequency, the resonant cavity performs as a spectral filter providing the signal enhancement according to FIG. 5.

The modulated light source input signal spectrum (1), consisting of Dirac's peaks, is matched to the resonant cavity spectrum (2) through its modulation frequency nm which has been adjusted to be equal to the free-spectral-range FSR of the cavity. This adjustment is independent of the gas/liquid absorption line/spectrum (3). The only requirement is that the resonant cavity FSR must be smaller than the absorption line width allowing wavelength modulation amplitude $\Delta\nu_m$ to be optimized for maximal sensitivity. The optimal wavelength modulation amplitude $\Delta\nu_m$ is in the same order of magnitude as the absorption line width (full-width at half-maximum).

This method is applied in the case of stable or stabilized cavity free-spectral-range which can be controlled through temperature for example. This method apply preferably strong resonant cavity for signal enhancement but optimal signal-to-noise ratio corresponds to the compromise between signal enhancement and system stability.

In the case of strongly varying cavity characteristics the first method is not applicable anymore and interferometric noise will be generated by the measurement cavity. Such a situation will occur when gas mixtures or temperature are unpredictable. It is often the case in transcutaneous blood gas detection.

An alternate method involves two steps, where modulation parameters comprising at least the modulation frequency and the frequency-modulation amplitude are determined in order to achieve strong interferometric noise rejection.

The first two parameters, modulation frequency and frequency-modulation amplitude, of the light source are set to initial values, called ideal values, defined as the values of the parameters which offer the maximal sensitivity to gas/liquid spectral characteristics, in the particular case where no interferometric noise is generated. These ideal values for the parameters are determined for each characteristic gas/liquid absorption spectral line.

In a second step, the case where a non negligible interferometric noise is generated by the measurement cavity, is addressed. An optimization procedure is performed: the initial values of the parameters are modified in a continuous way, in order to reach new values, called optimal values, defined as the values of the parameters which minimize the interferometric noise, while keeping the highest sensitivity to the spectral lines of the gas/liquid species.

As a consequence of this procedure, low interferences with the waveguide length and the effective refractive index variations can be achieved by the use of the optimized values of the modulation parameters. The latter result must be considered as a major achievement of the patent, because the determination of the optimal values of the modulation parameters also provides a large insensitivity of the concentration to the refractive index of the analyzed medium.

In a preferred embodiment the preferred waveguide length, which has been chosen for optimal sensitivity, is 14.5 cm and the refractive index 1.6 (not restricted to these values). The elimination of most of the irregularities along the optical path by a careful design of the optical circuit has been achieved and the measurement cavity formed by the measuring waveguide constitutes the dominant optical cavity, generating resonances characterized by a free-spectral-range (FSR) of 0.646 GHz, measured at the output system by sweeping the optical frequency of the light source 2 under stabilized cavity spectrum. Additional sweep of the modulation amplitude around ideal parameters set gives rise to a two-dimensional grid of resonances (Method One) illustrated by the simulation results shown in FIG. 6A. The bold black lines represent optimal situations in both optical frequency and modulation amplitude axis. As the interferometric noise consists of a random shift of the resonance along the optical frequency axis the interferometric noise can be seen as the standard deviation over the optical frequency range.

To illustrate this second method, FIG. 6B illustrates typical two-dimensional scan of the interferometric noise versus the modulation frequency and amplitude.

In the particular situation corresponding to the preferred embodiment, optimal situation takes place where noise (mainly from interferometric origin) is minimal. The dependence on the modulation amplitude is strong but weak on the modulation frequency. So the optimal parameters sets appears all along the bottom of the "valleys" giving more freedom on the modulation frequency choice.

In the preferred embodiment the modulation frequency is fixed to 200 MHz for electronic convenience without any restriction, then the optimal modulation amplitude is tuned at 4.85 GHz which is the nearest value around the ideal parameters set which modulation amplitude was 4.9 GHz.

Finally the optimal parameters set reached through the second method confers to the whole system an interferometric noise rejection so that system sensitivity can be considered as almost independent regarding to detected medium refractive index variations or waveguide length variations.

In summary, in addition to high selectivity and absorption baseline rejection due to modulation spectroscopy the achievements yielded by the second method are
a) high sensitivity due to optimal parameters set near the ideal parameters set
b) high interferometric noise rejection due to the determination of optimal parameters set
c) high signal-to-noise ratio (SNR) due to a) and b)
d) high independence towards waveguide length and effective refractive index variations due to b)
e) high independence towards detected medium refractive index variations due to d).

Considering all these advantages of the second method, applied after achievement of the first method, can be considered as an important innovation in gas/liquid sensing, especially in the absorption spectroscopy field and is applied to the preferred embodiment of the present invention.

The invention claimed is:

1. Sensor system for the detection of chemical substances in an adjacent medium, with
   an integrated optical waveguide adapted to produce an evanescent field for penetrating into the adjacent medium,
   wave-length-modulated light source means for coupling light into the waveguide, and
   detector means for receiving light from the waveguide and producing an output signal reflecting the sensed chemical substance, characterized by the fact that the waveguide has the form of a bifilar, non-crossing spiral consisting of an incoming or decreasing spiral segment and an outgoing or increasing spiral segment continuously bound by a pair of opposite central semi-circular segment.

2. A sensor system according to claim 1, characterized by an optical power splitter located between the light source and the waveguide for feeding an optical signal to the incoming segment of the waveguide and an optical reference signal.

3. A sensor system according to claim 2, characterized in that an optical output signal from the outgoing segment of the waveguide is fed together with the reference signal to the detector for balanced detection.

4. The sensor system according to claim 3, characterized by the fact that the waveguide is constituted by a multiplicity of individual spiral waveguides enlaced together forming a multiple non-crossing, cross-coupling-free spiral waveguide, whereby each individual waveguide associated with a different wavelength.

5. A sensor system according claim 3, characterized by the fact that the light source is wavelength-modulated and the detection circuitry is adapted for fundamental and/or harmonics detection.

6. The sensor system according to claim 2, characterized by the fact that the waveguide is constituted by a multiplicity of individual spiral waveguides enlaced together forming a multiple non-crossing, cross-coupling-free spiral waveguide, whereby each individual waveguide associated with a different wavelength.

7. A sensor system according claim 2, characterized by the fact that the light source is wavelength-modulated and the detection circuitry is adapted for fundamental and/or harmonics detection.

8. A sensor system according to claim 1 characterized by the fact that the waveguide is constituted by a multiplicity of individual spiral waveguides enlaced together forming a multiple non-crossing, cross-coupling-free spiral waveguide, whereby each individual waveguide associated with a different wavelength.

9. A sensor system according claim 8, characterized by the fact that the detection circuitry is adapted for fundamental and/or harmonics detection.

10. A sensor system according to claim 1, characterized by the fact that the detection circuitry is adapted for fundamental and/or harmonics detection.

11. A sensor system according to claim 1, characterized by the fact that the input and output fibers are elongated in such a way that the interferometric noise generated by these fibers can be eliminated.

12. A sensor system according to claim 1, characterized by the fact that the detector means comprise an opto-electronic detection circuit producing an output signal reflecting the sensed chemical substance.

13. Sensor system for the detection of chemical substances in an adjacent medium, comprising:
    an integrated optical waveguide adapted to produce an evanescent field for penetrating into the adjacent medium;
    light source means for coupling light into the waveguide; and
    an opto-electronic detection circuit for receiving light from the waveguide and producing an output signal reflecting the sensed chemical substance, characterized by the fact that the waveguide has the form of a bifilar, non-crossing spiral consisting of an incoming or decreasing spiral segment and an outgoing or increasing spiral segment continuously bound by a pair of opposite central semi-circular segment.

14. The sensor system of claim 13, wherein the light source means comprises:
    a wave-length-modulated light source means.

15. A sensor system according to claim 13 wherein input and output fibers are elongated in such a way that an interferometric noise generated by these fibers can be eliminated.

* * * * *